United States Patent
Amato

(10) Patent No.: US 10,343,984 B2
(45) Date of Patent: Jul. 9, 2019

(54) PROCESS FOR THE PREPARATION OF THE COMPOUND N-(3,5-DIMETHYLPHENYL)-N'-(2-TRIFLUOROMETHYLPHENYL) GUANIDINE

(71) Applicant: CHEMO RESEARCH, S.L., Madrid (ES)

(72) Inventor: José Amato, Buenos Aires (AR)

(73) Assignee: CHEMO RESEARCH. S.L., Madrid (ES)

( * ) Notice: Subject to any disclaimer, the term of this patent is extended or adjusted under 35 U.S.C. 154(b) by 0 days.

(21) Appl. No.: 15/751,437

(22) PCT Filed: Aug. 10, 2016

(86) PCT No.: PCT/EP2016/069033
§ 371 (c)(1),
(2) Date: Feb. 8, 2018

(87) PCT Pub. No.: WO2017/025560
PCT Pub. Date: Feb. 16, 2017

(65) Prior Publication Data
US 2018/0244608 A1    Aug. 30, 2018

(30) Foreign Application Priority Data

Aug. 11, 2015   (AR) .............................. 20150102582
Aug. 11, 2015   (EP) .................................... 15382424

(51) Int. Cl.
| | | |
|---|---|---|
| C07C 277/08 | (2006.01) | |
| C07C 277/02 | (2006.01) | |
| C07C 279/18 | (2006.01) | |
| C07C 277/06 | (2006.01) | |

(52) U.S. Cl.
CPC .......... C07C 277/02 (2013.01); C07C 277/06 (2013.01); C07C 277/08 (2013.01); C07C 279/18 (2013.01); C07B 2200/13 (2013.01)

(58) Field of Classification Search
CPC .... C07C 277/02; C07C 277/06; C07C 279/18
See application file for complete search history.

(56) References Cited

FOREIGN PATENT DOCUMENTS

| EP | 2766342 B1 | 2/2016 |
|---|---|---|
| WO | WO 2013/053726 A1 | 4/2013 |

OTHER PUBLICATIONS

Feng-Qi et al. Chinese Journal of Chemistry, 2008, vol. 26(8), pp. 1481-1485 (Year: 2008).*
International Search Report and Written Opinion dated Oct. 31, 2016 for PCT/EP2016/069033, 10 pages.

* cited by examiner

*Primary Examiner* — Nyeemah A Grazier
(74) *Attorney, Agent, or Firm* — Squire Patton Boggs (US) LLP

(57) ABSTRACT

The present invention relates to a process for the preparation of the compound N-(3,5-dimethylphenyl)-N'-(2-trifluoromethylphenyl) guanidine of formula (I) which comprises reacting a salt of a compound of formula (II) or a mixture of the salt of the compound of formula (II) and a compound of formula (II) with a compound of formula (III), in the presence of a polar organic solvent; a crystalline solid form of the compound of formula (I), in particular crystalline solid form A; to a pharmaceutical composition comprising them; and to their use as a medicament, in particular to the treatment of a condition mediated by Rho-GTPase cell proteins.

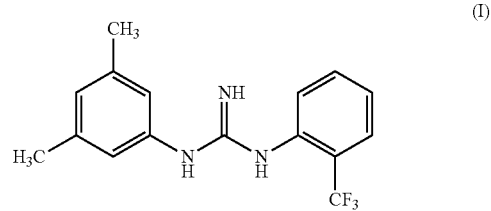

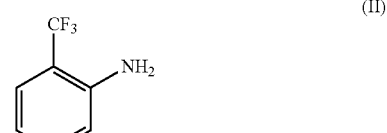

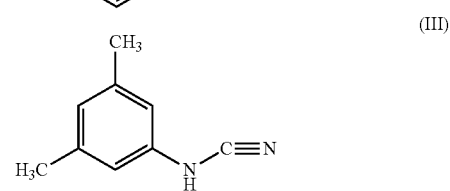

13 Claims, 4 Drawing Sheets

PROCESS FOR THE PREPARATION OF THE COMPOUND N-(3,5-DIMETHYLPHENYL)-N'-(2-TRIFLUOROMETHYLPHENYL) GUANIDINE

The present invention relates to a process for the preparation of the compound N-(3,5-dimethylphenyl)-N'-(2-trifluoromethylphenyl) guanidine of formula (I). It also relates to a process for the preparation of a crystalline solid form of the compound of formula (I), particularly to a crystalline solid form A, and to a pharmaceutically composition containing them. It also relates to the crystalline solid form of the compound of formula (I) for use as a medicament, in particular for the treatment of a condition mediated by Rho-GTPase cell proteins.

BACKGROUND ART

Rho family GTPase are molecular switches that control signaling pathways regulating actin cytoskeleton reorganization, gene expression, cell cycle progression, cell survival, and other cellular processes. Among other functions, they participate in cell cycle and cell division regulation, being also involved in secretion, endocytosis, phagocytosis, membrane traffic and apoptosis. Rho family proteins constitute one of three major branches of the Ras superfamily. Rho proteins share approximately 30 percent amino acid identity with the Ras proteins. At least 23 mammalian Rho family proteins have been identified thus far, including RhoA, Rac1 and Cdc42.

Tumor cells, besides presenting proliferation deregulation, they present alterations in their morphological characteristics and, in the case of metastasis, and they get the ability to pass through tissue barriers. Rho-GTPases play an important role in controlling cell morphology and motility. A compound capable of specifically inhibiting Rho-GTPases activity offers a specific alternative in cancer therapy.

The compound N-(3,5-dimethylphenyl)-N'-(2-trifluoromethylphenyl) guanidine represented by the structural formula (I) is a potent and selective inhibitors of Rho-GTPase cell proteins:

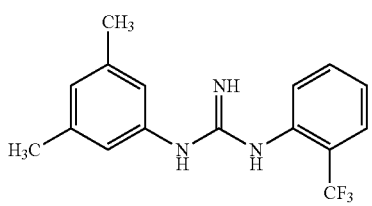

(I)

Particularly, the compound of formula (I) can be used to inhibit Rho-related Rac1 GTPase cell protein. Accordingly, the compound of formula (I) as an inhibitor of the Rho-related Rac1 GTPase cell protein can be used to treat diseases mediated by mammalian Rac1 cell proteins, particularly for the treatment of any condition mediated by Rho-GTPase cell proteins such as Rac1 cell proteins.

The preparation and the therapeutic use of the compound of formula (I) has been described in the European Patent number EP2766342.

EP2766342 discloses a process for the preparation of the compound 25 (cf. Example 1) which corresponds to the compound of formula (I) of the present invention. The process disclosed in EP2766342 comprises reacting equimolar amounts of a solution of 3,5-dimethylaniline chlorhydrate and N-(2-trifluoromethyl)phenyl)cyanamide in absolute ethanol at a reflux temperature for 15 h. The crude compound of formula (I) was purified by column chromatography with a mixture of hexane and ethyl acetate in the presence of triethylamine. The purified compound of formula (I) was obtained as a white solid compound showing a melting point of 127° C. However, the European patent EP2766342 does not disclose a process for preparing a crystalline solid form of the compound of formula (I). Furthermore, the use of extreme reaction conditions for a prolonged period of time and the use of non-scaling purification technics such as chromatography causes considerable difficulties for its industrial scale up.

On the other hand, polymorphism is the property of some molecules to assume more than one crystalline form in the solid form. A single molecule may give rise to a variety of crystalline forms (also called "polymorphs") having distinct physical properties. The existence and physical properties of different crystal forms can be determined by a variety of techniques such as X-ray diffraction spectroscopy, differential scanning calorimetry, infrared spectroscopy and melting point. Differences in the physical properties of different crystalline solid forms result from the orientation and intermolecular interactions of adjacent molecules in the bulk solid. Accordingly, polymorphs are distinct solids sharing the same molecular formula yet having distinct advantageous and/or disadvantageous physical properties compared to other forms in the polymorph family. The existence and physical properties of polymorphs is unpredictable.

One of the most important physical properties of a pharmaceutical compound which can form polymorphs is its solubility in aqueous solution, particularly the solubility in gastric juices of a patient. Other important properties relate to stability, bioavailability, ease of formulation, ease of administration, among others. Since some of the crystalline solid form are more adequate for one type of formulation, and other forms for other different formulations, the development of new crystalline solid forms, such as for example crystalline solid forms (i.e. polymorphs), allows for improving the characteristics of the pharmaceutical formulations comprising them. In addition, depending on the therapeutic indications, one or another pharmaceutical formulation may be preferred.

Especially desirable improvements/advantages of a crystalline solid form of the compound of formula (I) form would include: improvement of physicochemical properties in order to facilitate its manufacture or its formulation; to enhance the absorption and/or the bioavailability; being easily obtainable with more constant physicochemical properties; allowing more flexibility while formulating, or facilitating its formulation; having better dispensability properties, thus allowing better dispersion rates, especially if dispersed in an aqueous physiological surrounding, or reducing hygroscopicity; improving stability; and allowing new routes of administration. Most desirably the new crystalline solid form should combine more than one, or even most of these advantages.

Thus, there is a need to develop a more economical and more easily industrializable process for the preparation of the compound of formula (I), in particular for the preparation of new crystalline solid form of the compound of formula (I) suitable for use in the pharmaceutical industry and, in particular, for the treatment of a condition mediated by Rho-GTPase cell proteins.

SUMMARY OF THE INVENTION

Inventors have found a new process for the preparation of the compound of formula (I) which comprises reacting a salt of an aniline compound of formula (II) with a cyanamide compound of formula (III) under mild temperature and for a short period of time. It is advantageous because the process comprises the use of commercially available or easily preparable starting materials which allows an easier industrial scaling up.

Furthermore, the process of the invention is carried out under reaction conditions that allow obtaining a compound of formula (I) in crude form having an impurity profile which is easily purifiable by recrystallization. Particularly, the process of the invention allows obtaining crude of the compound of formula (I) in crystalline solid form.

Additionally, it can be obtained as a crystalline solid form A, both by crystallization from the reaction media or by recrystallization in specific conditions. It is advantageous because the crystalline solid form A of compound (I) has the appropriate physical and chemical properties for its use in the pharmaceutical industry.

Thus, the first aspect of the present invention relates to a process for the preparation of the compound N-(3,5-dimethylphenyl)-N'-(2-trifluoromethylphenyl) guanidine of formula (I),

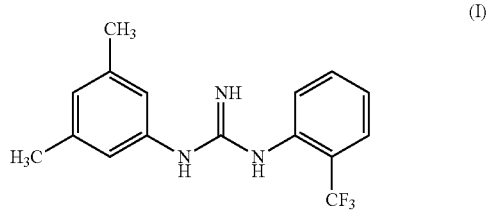
(I)

which comprises reacting a salt of a compound of formula (II) or a mixture of the salt of the compound of formula (II) and a compound of formula (II)

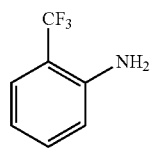
(II)

with a cyanamide compound of formula (III),

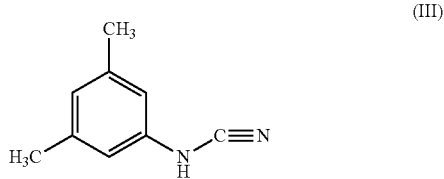
(III)

in the presence of a polar organic solvent.

The second aspect of the invention is a crystalline solid form A of the compound N-(3,5-dimethylphenyl)-N'-(2-trifluoromethylphenyl) guanidine of formula (I), which shows a melting point of 131.5° C.

The third aspect of the invention is a pharmaceutical composition comprising a therapeutically effective amount of a crystalline solid form A of the compound N-(3,5-dimethylphenyl)-N'-(2-trifluoromethylphenyl) guanidine of formula (I) of the present invention, together with one or more pharmaceutically acceptable excipients or carriers.

The fourth aspect of the invention is the crystalline solid form A of the compound N-(3,5-dimethylphenyl)-N'-(2-trifluoromethylphenyl) guanidine of formula (I) of the present invention, for use as a medicament.

The fifth aspect of the invention is the crystalline solid form A of the compound N-(3,5-dimethylphenyl)-N'-(2-trifluoromethylphenyl) guanidine of formula (I) of the present invention, for use in the treatment of a condition mediated by Rho-GTPase cell proteins.

DETAILED DESCRIPTION OF THE INVENTION

Figure 1:
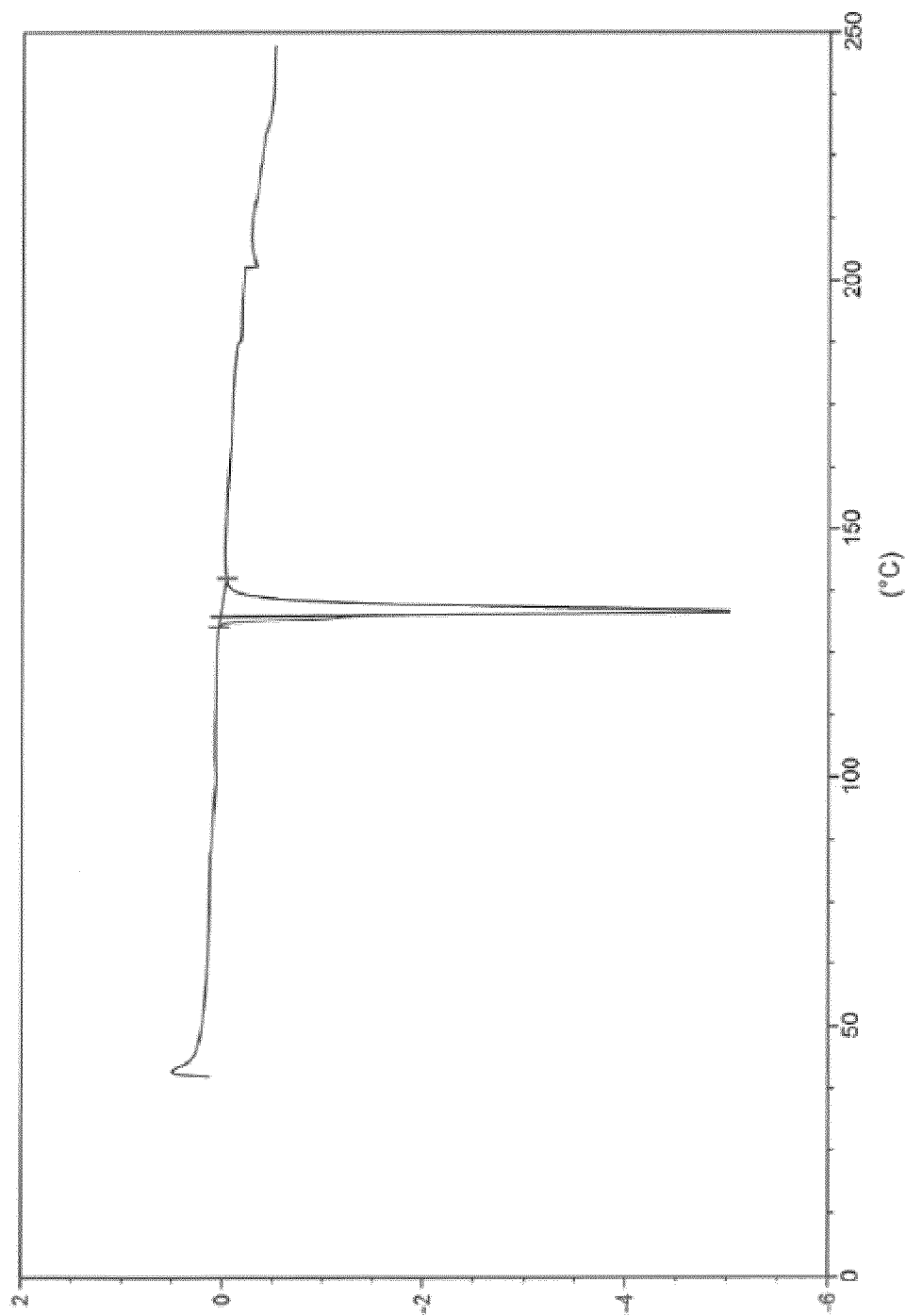
FIG. 1 shows the DSC curve of the crystalline solid form A of the compound of formula (I) of the present invention. The spectrum expresses the heat flow (W/g) versus temperature (° C.).

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "room temperature" refers to a temperature comprised from 20° C. to 25° C.

As mentioned above, an aspect of the present invention refers to a process for the preparation of the compound of formula (I). The process is carried out under such as conditions that allow obtaining a compound of formula (I) in crystallized crude form easily purificable by recrystallization.

In an embodiment of the invention, optionally in combination with one or more features of the various embodiments described above or below, the process comprises reacting a salt of the aniline compound of formula (II) with a cyanamide compound of formula (III) in the presence of a polar organic solvent.

In an alternative embodiment of the invention, optionally in combination with one or more features of the various embodiments described above or below, the process comprises reacting a mixture of the aniline compound of formula (II) and a salt of the aniline compound of formula (II) with a cyanamide compound of formula (III) in the presence of a polar organic solvent.

In an embodiment of the invention, optionally in combination with one or more features of the various embodiments described above or below, the salt of the compound of formula (II) is an inorganic salt; preferably a halohydrate salt selected from the group consisting of chlorhydrate, bromhydrate and iodide hydrate; more preferably the salt of the compound of formula (II) is a chlorhydrate salt.

In an embodiment of the invention, optionally in combination with one or more features of the various embodiments described above or below, the polar organic solvent is selected from a ($C_1$-$C_3$) alcohol and a mixture of ($C_1$-$C_3$) alcohol and water. The term "alcohol" refers to a hydrocarbon in which one or more hydrogen atoms have been replaced by one or more —OH group. The hydrocarbon contains the number of carbon atoms specified in the description or claims. The term alcohol also includes glycol compounds.

In an embodiment of the invention, optionally in combination with one or more features of the various embodiments described above or below, the polar organic solvent is a ($C_1$-$C_3$) alcohol selected form the group consisting of ethanol, 2-propanol (i.e., isopropanol) and n-propanol; preferably ethanol; and most preferably, absolute ethanol.

In an embodiment of the invention, optionally in combination with one or more features of the various embodiments described above or below, the polar organic solvent is a mixture of ($C_1$-$C_3$) alcohol and water; preferably ethanol and water. In an embodiment of the invention, optionally in combination with one or more features of the various embodiments described above or below, the polar organic solvent is a mixture of ethanol and water, wherein the mixture comprises 83% by volume of ethanol and 17% by volume of water. In the context of the invention, the term "% by volume" refers to the percentage of volume of each solvent (i.e. ethanol and water) needed to promote the preparation of the compound of formula (I). The use of a mixture of a mixture of ($C_1$-$C_3$) alcohol and water as a polar organic solvent is advantageous because allows reducing the economical cost of the process.

Advantageously, in comparison with the process disclosed in the state of the art, the starting material in combination with the reaction conditions of the process allows obtaining a crude compound of formula (I) having an appropriate impurity profile for being easily crystalized. Unlike as described in the state of the art, the crude compound of formula (I) of the present invention has an impurity profile that allows removing the impurities by recrystallization. Furthermore, the purified compound of formula (I) is in crystalline form having an impurity profile that complies with the mandatory requirements of the pharmaceutical industry.

In an embodiment of the invention, optionally in combination with one or more features of the various embodiments described above or below, the process of the invention is carried out at a temperature comprised from 60° C. to 75° C.; preferably from 65° C. to 72° C. In an embodiment of the invention, optionally in combination with one or more features of the various embodiments described above or below, the process is carried out at a 70° C.

The starting materials (II) and (III) are commercially available or can be prepared by any method known in the state of the art. In an embodiment, optionally in combination with one or more features of the various embodiments described above or below, the process of the invention as defined above further comprises a previous step of reacting a compound 3,5-dimethylphenyl thiourea of formula (IV) under such reaction conditions that lead to a compound of formula (III), using KOH and $(CH_3COO)_2Pb \cdot 3H_2O$ as shown in the following scheme:

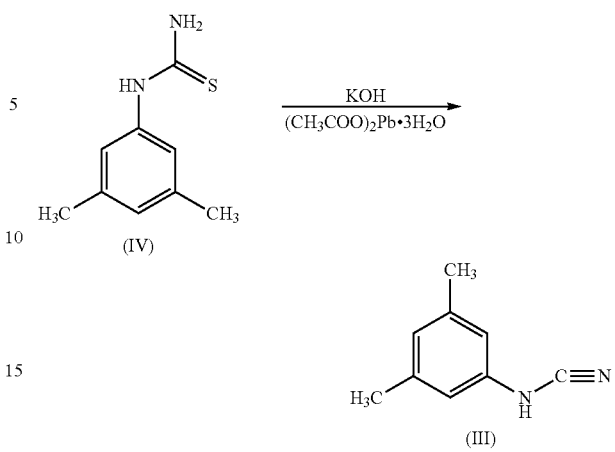

The starting material (IV) is also commercially available or can be prepared by any method known in the state of the art.

It is also part of the invention a process for the preparation of the compound N-(3,5-dimethylphenyl)-N'-(2-trifluoromethylphenyl) guanidine of formula (I) as defined above, which further comprises an additional step of crystallizing the compound of formula (I) to obtain a crystalline solid form.

Crystallization is a process of formation of solid crystals from a homogeneous solution that involves a chemical solid-liquid separation technique, in which mass transfer of a solute from the liquid solution to a pure crystalline solid phase occurs. The term "crystal" or "crystalline solid" or "crystal solid form" is a solid material whose constituents are arranged in a highly ordered microscopic structure, forming a crystal lattice that extends in all directions. In addition, macroscopic single crystals are usually identifiable by their geometrical shape, consisting of flat faces with specific, characteristic orientations.

The preparation of the crystalline solid form of the compound of formula (I) can be carried by any technic known in the state of the art. For example, by forming a solvent solution containing the compound of formula (I) and inducing precipitation of crystalline solid form of the compound of formula (I) by cooling, by adding an anti-solvent or by adding seeds of the compound of formula (I).

The selection of the crystallization conditions is crucial for determining the crystalline solid form of the compound of formula (I) and its physical and chemical characteristics.

In an embodiment of the invention, optionally in combination with one or more features of the various embodiments described above or below, the process comprises crystallizing the crude compound of formula (I) from a mixture of a ($C_1$-$C_3$) alcohol and water; preferably the ($C_1$-$C_3$) alcohol is ethanol. In a preferred embodiment, optionally in combination with one or more features of the various embodiments described above or below, the process comprises crystallizing the crude compound of formula (I) from a mixture of a ($C_1$-$C_3$) alcohol and water, wherein the mixture comprises 83% by volume of ethanol and 17% by volume of water. In the context of the invention, the term "% by volume" refers to the percentage of volume of each solvent (i.e. ethanol and water) needed to promote the preparation of the crystalline form A of the compound of formula (I). In these conditions, the crystalline form obtained is the crystalline form A. Crystalline form A can be obtained directly from the reaction media using the conditions specified above or by carrying out a recrystallization in such conditions.

The second aspect of the invention is a crystalline solid form A of the compound N-(3,5-dimethylphenyl)-N'-(2-trifluoromethylphenyl) guanidine of formula (I) of the present invention, which shows a melting point of 131.5° C. As it is disclosed in the Examples, the $^1$H RMN spectrum, $^{13}$C RMN spectrum, mass spectroscopy and elemental analysis of the crystalline solid form A of the compound of formula (I) of the present invention corresponds to the compound 25 disclosed in the European Patent application number EP2766342.

The crystalline solid form A of the compound of formula (I) is that which shows in the differential scanning calorimetry (DSC) a endothermic phenomenum with a pick at 132.42° C. having a associated heat of 80.37 J/g. The crystalline solid form A is that which has the differential scanning calorimetry diagram showed in FIG. 1. This curve differs from the curve of the crystalline solid forms of the compound of formula (I) known in the state of the art.

Figure 2:
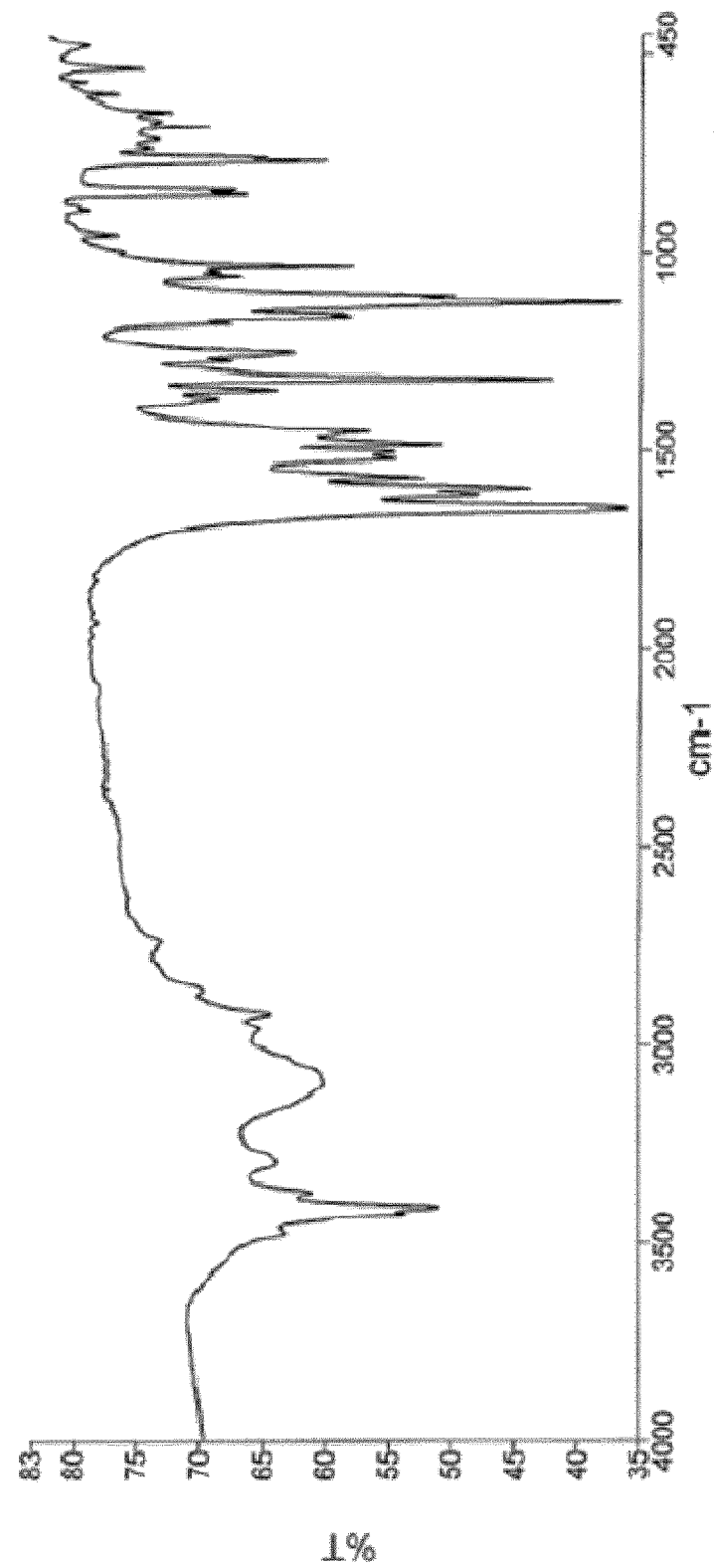
FIG. 2 shows the infrared spectrum of the crystalline solid form A of the compound of formula (I) of the present invention. The curve expresses the transmittance (T) versus the wavenumber value ($cm^{-1}$).

The crystalline solid form A of the compound of formula (I) also shows an infrared spectrum that comprises characteristic peaks at 3477, 3430, 3416, 3371, 3299, 3084, 2925, 1649, 1615, 1596, 1519, 1503, 1483, 1316, 1123, 1107, 1033, 850, 764. The crystalline solid form A is that which has the infrared spectrum showed in FIG. 2. This spectrum differs from the spectrum of the crystalline solid form of the compound of formula (I) known in the state of the art.

In an embodiment of the invention, optionally in combination with one or more features of the various embodiments described above or below, the crystalline solid form A of the compound of formula (I) may be defined by its preparation process as defined above and therefore, the crystalline solid form A of the compound of formula (I) obtainable by the process of the invention is considered part of the invention. Thus, the crystalline solid form A of the compound of formula (I) obtainable by the process comprising reacting a salt of a compound of formula (II) or a mixture of the salt of the compound of formula (II) and a compound of formula (II) with a cyanamide compound of formula (III), in the presence of a polar organic solvent, optionally followed by an additional step of recrystallizing the compound of formula (I). For the purposes of the invention the expressions "obtainable", "obtained" and equivalent expressions are used interchangeably, and in any case, the expression "obtainable" encompasses the expression "obtained".

The third aspect of the invention relates to a pharmaceutical composition comprising a therapeutically effective amount of a crystalline solid form A of the compound N-(3,5-dimethylphenyl)-N'-(2-trifluoromethylphenyl) guanidine of formula (I) of the present invention, together with one or more pharmaceutically acceptable excipients or carriers.

The expression "therapeutically effective amount" as used herein, refers to the amount of the compound of formula (I) that, when administered, is sufficient to prevent development of, or alleviate to some extent, one or more of the symptoms of the disease which is addressed. The particular dose of the compound of formula (I) administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

Compositions of the present invention can be prepared according to methods well known in the state of the art. The appropriate excipients and/or carriers, and their amounts, can readily be determined by those skilled in the art according to the type of formulation being prepared.

The fourth aspect of the invention is the crystalline solid form A of the compound N-(3,5-dimethylphenyl)-N'-(2-trifluoromethylphenyl) guanidine of formula (I) of the present invention, for use as a medicament.

In an embodiment, optionally in combination with one or more features of the various embodiments described above or below, the crystalline solid form A of the compound N-(3,5-dimethylphenyl)-N'-(2-trifluoromethylphenyl) guanidine of formula (I) as defined above, for use in the treatment of a condition mediated by Rho-GTPase cell proteins, particularly by Rac1 cell proteins.

This aspect could be also formulated as the use of the pharmaceutical composition as defined above for the preparation of a medicament for the prophylaxis and/or treatment of a condition mediated by Rho-GTPase cell proteins, particularly by Rac1 cell proteins. It also relates to a method for the prophylaxis and/or treatment of a mammal suffering or is susceptible to suffer from a condition mediated by Rho-GTPase cell proteins, particularly by Rac1 cell proteins, the method comprises administering to said mammal an effective amount of the pharmaceutical composition of the present invention.

Throughout the present specification, by the term "treatment" is meant eliminating, reducing or ameliorating the cause, the effects or progression of a condition; and includes a reduction in the rate of progress, a halt in the rate of progress, amelioration of the condition, and cure of the condition. Treatment as a prophylactic measure (e.g., prophylaxis) is also included. The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies as in immunotherapy), prodrugs (e.g., as in photodynamic therapy, GDEPT, ADEPT, etc.); surgery; radiation therapy; and gene therapy. For purposes of this invention treatment includes, but is not limited to, alleviation, amelioration or elimination of one or more symptoms of the condition; diminishment of the extent of the condition; stabilized (i.e. not worsening) state of condition; delay or slowing of condition progression; amelioration or palliation of the condition state; and remission of the condition (whether partial or total).

The compound of formula (I) of the invention is Rho-GTPase cell protein, more specifically Rac1 cell protein, inhibitors, being useful in the treatment of a condition mediated by Rho-GTPase cell protein, preferably a condition mediated by Rac1 cell protein.

The term "a disease mediated by Rac1 cell protein", as used herein pertains to a condition in which Rac1 cell protein and/or the action of Rac1 is important or necessary, e.g., for the onset, progress, expression, etc. of that condition.

Since Rho-GTPases kinases are known to have a central role in the cell cycle, and in particular Rac1, in a preferred embodiment of the present invention the diseases, conditions and/or disorders, which can be prevented, ameliorated or treated with the compounds of the present invention are proliferative diseases. A disease is considered to benefit from reduced Rho-GTPase, in particular Rac1 activity, if a reduction of Rac1 activity of at least 10%, preferably of at least 20%, preferably of at least 30%, leads to an improvement of at least one clinical indicator of that disease. Examples of such indicators are proliferation rate, which is preferably reduced, cellular differentiation, which is preferably induced etc.

It is further preferred that the proliferative diseases are selected from the group consisting of precancerosis; dysplasia; metaplasia; carcinomas of the gastrointestinal or colorectal tract, liver, pancreas, kidney, bladder, prostate, endometrium, ovary, testes, melanoma, dysplastic oral mucosa, invasive oral cancers, small cell and non-small cell lung carcinomas, hormone-dependent breast cancers, hormone-independent breast cancers, transitional and squamous cell cancers, neurological malignancies including neuroblastoma, gliomas, glioblastoma, astrocytomas, osteosarcomas, soft tissue sarcomas, hemangiomas, endocrinological tumours, hematologic neoplasias including leukemias, lymphomas, and other myeloproliferative and lymphoproliferative diseases, carcinomas in situ, hyperplastic lesions, adenomas, fibromas, histiocytosis, chronic inflammatory proliferative diseases, vascular proliferative diseases and virus-induced proliferative diseases, skin diseases characterized by hyperproliferation of keratinocytes and/or T cells. Particular preferred diseases treatable with the compounds of the present invention are glioblastoma; and colorectal, ovarian, prostatic and gastric cancers and adenocarcinomas, more preferably invasive adenocarcinomas.

Thus, the present invention also provides active compounds which are antiproliferative agents. The term "antiproliferative agent" as used herein, refers to a compound which treats a proliferative condition (i.e., a compound which is useful in the treatment of a proliferative condition).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human. Preferably, the subject is a human.

The treatment defined hereinbefore may be applied as a sole therapy or may involve, in addition to the compound of formula (I) of the invention, conventional surgery or radiotherapy or chemotherapy.

Throughout the description and claims the word "comprises" and variations of the word, are not intended to exclude other technical features, additives, components or steps. Additional objects, advantages and features of the invention will become apparent to those skilled in the art upon examination of the description or may be learned by practice of the invention. The following examples and drawings are provided by way of illustration, and they are not intended to be limiting of the present invention.

EXAMPLES

All reagents were commercially available. Melting points were measured with a Buchi mod B-545. $^1$H and $^{13}$C NMR spectra were recorded on a Varian spectrometer VNMRS-500. The elemental analysis was recorded on a LECO CHNS-932. Mass spectroscopy spectra were recorded on Lc/MS DVL agilent technologies using the technic API-ES (Atmospheric Pressure ionization-electrospray) in positive mode. IR spectra were recorded on a Spectrum One FT-IT by potassium bromide discs (2 mg/300 mg). The DSC spectra were recorded on a TA Instruments Mod. Q20. DSC measurements require that samples (1 g and 1.5 g) were enclosed in a aluminium pan which is then sealed and heated from 40° C. to 250° C. at a rate of 10° C./min.

Example 1

Crystalline Solid Form A of the Compound N-(3,5-dimethylphenyl)-N'-(2-trifluoromethylphenyl) guanidine of Formula (I)

Step A. Preparation of 3,5-dimethylphenyl thiourea of Formula (IV)

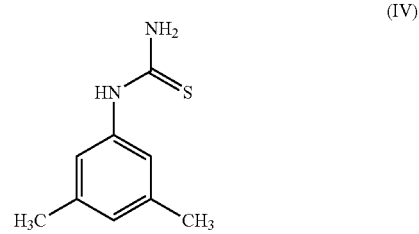

(IV)

To a mixture of 3,5-dimethyl aniline (V) (Aldrich) (194 g) and water (800 ml) with stirring, HCl (192 g) was slowly added at room temperature. The resulting mixture was stirred for 15 minutes. Then, ammonium thiocyanate (VI) (Biopack) (134 g) was added at room temperature. The resulting mixture was heated at 96° C. for 15 hours with stirring. After that time, the mixture was cooled with stirring until 25° C. and was maintained at a temperature between 20° C. and 25° C. with stirring overnight. The obtained precipitate was filtered under vacuum, rinsed with water and dried to obtain the crude 3,5-dimethylphenyl thiourea of formula (IV) (235 g).

The crude compound of formula (IV) was dissolved in hot ethanol (96%, 1.4 L) and to the resulting mixture, hot toluene (450 ml) was added. The precipitate was stirred overnight at 25° C. After that time, the precipitate was filtered, rinsed with cool ethanol (96%), and dried with air followed under vacuum to obtain the compound of formula (IV) as crystalline solid form (156 g; m.p. 170-172° C.).

Step B. Preparation of 3,5-dimethylphenylcyanamide of Formula (III)

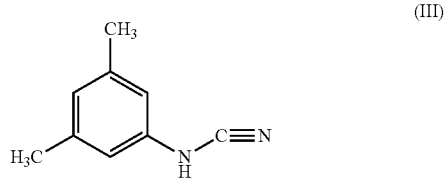

(III)

Solutions A-C were prepared: Solution A was prepared by dissolving 3,5-dimethylphenyl thiourea of formula (IV) (72 g; 0.4 mol) in water (300 ml). Solution B was prepared by dissolving KOH (224 g) in water (600 ml). Solution C was prepared by dissolving (CH$_3$COO)$_2$Pb.3H$_2$O (167 g) in water (200 ml). Then, solutions A-C were stored at 95° C. with stirring.

To the solution A, the solution B at 95° C. was added with stirring followed immediately by the addition of solution C at 95° C. with stirring. A precipitate was formed and the resulting mixture was heated at reflux temperature for 2 minutes. After that time, the mixture was cooled at 0° C. The mixture was filtered, acidified by the addition of acetic acid (260 ml) and rinsed with cool water (×6 portions). Then, the mixture was filtered and dried under vacuum to obtain the compound of formula (III) (53 g).

The compound of formula (III) was dissolved in hot toluene (200 ml). Then, activated carbon was added and the resulting mixture was filtered through a bed of preheated dicalite. After that, 60 ml hot n-hexane was added, and the mixture was cooled and crystalized at 0° C. The crystals were dried with air followed by vacuum to obtain the compound of formula (III) as white crystalline solid form (34 g; 58% yield, m.p. 118-120° C.).

Step C. Preparation of Crystalline Solid Form A N-(3,5-dimethylphenyl)-N'-(2-trifluoromethylphenyl) guanidine of Formula (I)

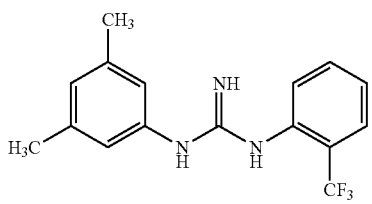

To a mixture of the 2-trifluoromethylaniline chlorhydrate of formula (II-HCl) (Aldrich) (15 g, 0.076 mol) and 2-trifluoromethylaniline of formula (II) (6 g, 0.037 mol) (Aldrich) in absolute ethanol (145 ml) and water (30 ml), 3,5-dimethylphenylcyanamide of formula (III) (3 g, 0.0163) was added. The resulting mixture was heated to 60° C. with stirring, and 3,5-dimethylphenylcyanamide of formula (III) (10.2 g, 0.0556) was slowly added during 1 hour at 60° C. with stirring.

The resulting mixture was heated at 70° C. for 1 hour. After that time, the mixture was cooled at 15° C. and NaOH 1N (aprox. 71 g) was added with stirring until pH 9.0. The mixture with the compound of formula (I) was stored at 0° C. for 15 hours. The solid was filtered and dried to obtain the crude crystalline compound of formula (I) (4.8 g; 21% yield, ≥98% HPLC).

The crude crystalline compound of formula (I) was recrystallized from a mixture of ethanol/water to obtain the compound of formula (I) as a white crystalline solid form A.

$^1$H RMN (500 MHz, CDCl$_3$) δ 7.61 (d, J=6.8 Hz, 1H), 7.44.7.41 (m, 1H), 7.07-7.04 (m, 2H), 6.81 (s, 2H), 6.73 (s, 1H), 4.31 (sa, 2H), 2.25 (s, 6H). $^{13}$C RMN (500 MHz, CDCl$_3$) 149.3, 147.7, 139.0, 132.8, 126.8 (q, J=5.3 Hz), 125.8, 125.2 124.3 8q, J=273 Hz), 123.8 (q, J=28.7 Hz), 122.0, 120.2 21.2. IR (cm-1) 3477, 3430, 3416, 3371, 3299, 3084, 2925, 1649, 1615, 1596, 1519, 1503, 1483, 1316, 1123, 1107, 1033, 850, 764. EM (u.m.a.) [M+H]+=308. Anal. Calcd. For C$_{16}$H$_{16}$F$_3$N$_3$: % C, 62.53; % H, 5.25; % N, 13.67. Found: % C, 62.36; % H; 5.06; % N, 13.71. m. p.: 131.6-131.7° C. DSC (Tonset)=132.42° C.

Example 2

Comparative Solid Form of the Compound N-(3,5-dimethylphenyl)-N'-(2-trifluoromethylphenyl) guanidine of Formula (I)

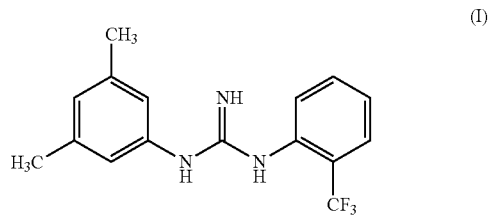 [SMILES: Cc1cc(C)cc(NC(=N)Nc2ccccc2C(F)(F)F)c1]

The comparative solid form of the compound of formula (I) was prepared following the process disclosed in Example 1 for compound 25 of the European Patent Application EP2766342. This process comprises reacting equimolar amounts of a solution of 3,5-dimethylaniline chlorhydrate and N-(2-trifluoromethyl)phenyl)cyanamide in absolute ethanol at a reflux temperature for 15 h. An aqueous solution of NaOH was added until pH 9. The mixture was extracted with dichloromethane. Organic phases were dried with Na$_2$SO$_4$ and filtered. The solvent was evaporated to obtain the compound of formula (I) in crude solid form. The crude was purified by column chromatography with a hexane:ethyl acetate gradient in presence of triethylamine to obtain pure solid form of the compound of formula (I).

Figure 3:
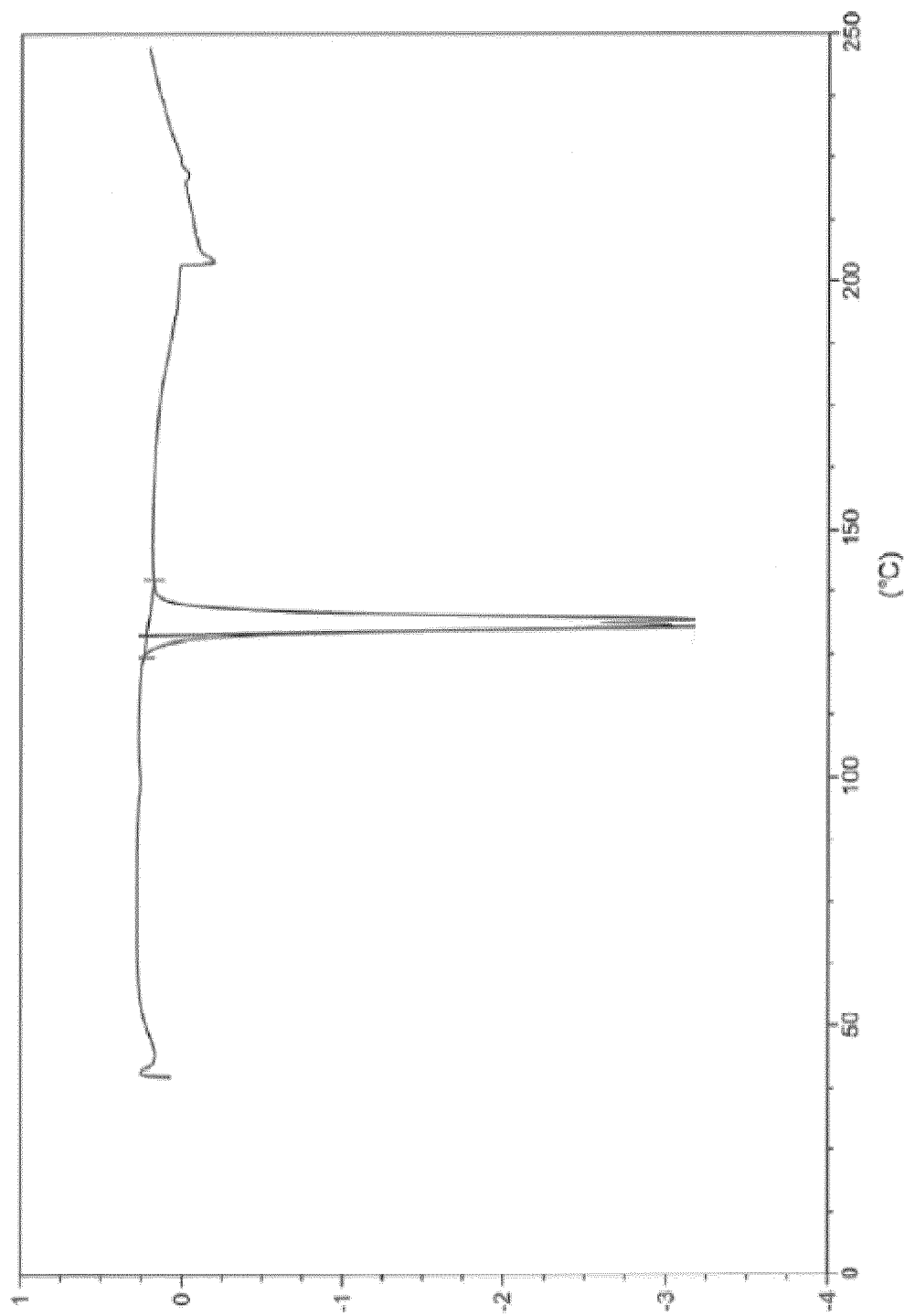
FIG. 3 shows the DSC curve of the comparative crystalline solid form of the compound of formula (I) known in the state of the art. The spectrum expresses the heat flow (W/g) versus temperature (° C.).
Figure 4:
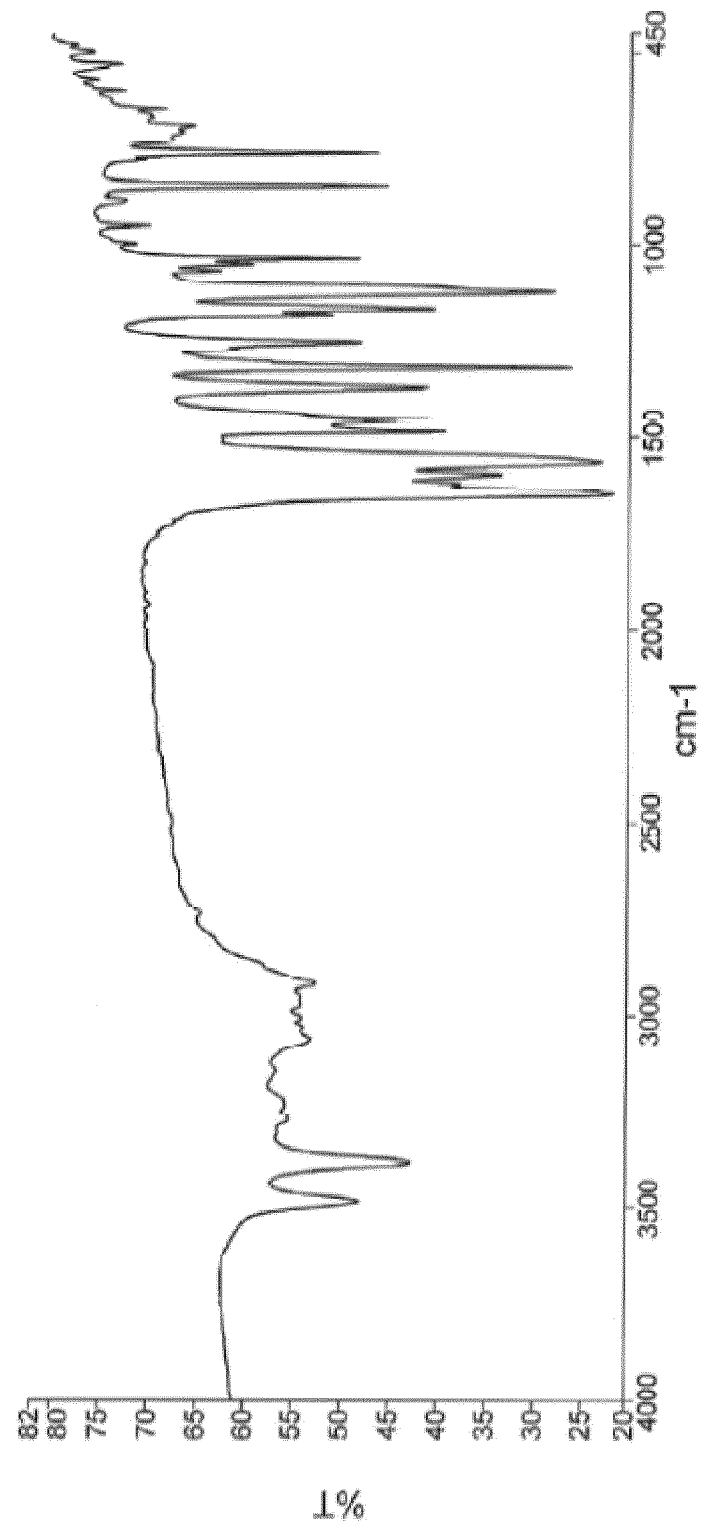
FIG. 4 shows the infrared spectrum of the comparative crystalline solid form of the compound of formula (I) known in the state of the art. The curve expresses the transmittance (T) versus the wavenumber value ($cm^{-1}$).

$^1$H RMN (500 MHz, CDCl$_3$) δ 7.61 (d, J=6.8 Hz, 1H), 7.44.7.41 (m, 1H), 7.07-7.04 (m, 2H), 6.81 (s, 2H), 6.73 (s, 1H), 4.32 (sa, 2H), 2.25 (s, 6H). IR (cm$^{-1}$) 3486, 3382, 3278, 3228, 3060, 2917, 1651, 1597, 1562, 1483, 1454, 1370, 1320, 1251, 1167, 1117, 1033, 841, 757 (showed in FIG. 4). EM (u.m.a.) [M+H]$^+$=308. Anal. Calcd. For C$_{16}$H$_{16}$F$_3$N$_3$: % C, 62.53; % H, 5.25; % N, 13.67. Found: % C, 62.51; % H; 5.08; % N, 13.63. m.p.: 129.4-129.5° C. DSC (T$_{onset}$) =128.78° C. (showed in FIG. 3).

The invention claimed is:

1. A process for the preparation of a crystalline solid form A of the compound N-(3,5-dimethylphenyl)-N'-(2-trifluoromethylphenyl) guanidine of formula (I),

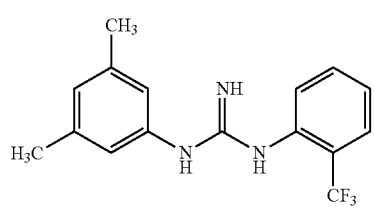

showing a DSC of 132.4° C., which comprises reacting a salt of a compound of formula (II) or a mixture of the salt of the compound of formula (II) and a compound of formula (II)

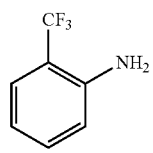

(II)

with a cyanamide compound of formula (III),

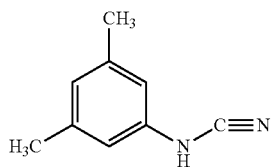

(III)

in the presence of a polar organic solvent.

2. The process according to claim 1, wherein the process is carried out by reacting a mixture of a compound of formula (II) and a salt of a compound of formula (II) with a cyanamide compound of formula (III).

3. The process according to claim 1, wherein the salt of the compound of formula (II) is the chlorhydrate salt of the compound of formula (II).

4. The process according to claim 1, wherein the polar organic solvent is ($C_1$-$C_3$) alcohol.

5. The process according to claim 4, wherein the ($C_1$-$C_3$) alcohol is ethanol.

6. The process according to claim 1, wherein the reaction is carried out at a temperature comprised from 60° C. to 75° C.

7. The process according to claim 1, further comprising an additional step of crystallizing the compound of formula (I).

8. The process according to claim 7, wherein the crystallization is carried out in the presence of a mixture of ($C_1$-$C_3$)alcohol and water.

9. A crystalline solid form A of the compound N-(3,5-dimethylphenyl)-N'-(2-trifluoromethylphenyl) guanidine of formula (I) showing a melting point of 131.5° C.

10. The crystalline solid form A of formula (I) according to claim 9, showing a DSC of 132.4° C.

11. A pharmaceutical composition comprising a therapeutically effective amount of the crystalline solid form of the compound N-(3,5-dimethylphenyl)-N'-(2-trifluoromethylphenyl) guanidine of formula (I) as defined in claim 9, together with one or more pharmaceutically acceptable excipients or carriers.

12. The crystalline solid form A of the compound N-(3,5-dimethylphenyl)-N'-(2-trifluoromethylphenyl) guanidine of formula (I) as defined in claim 9, for use as a medicament.

13. The crystalline solid form A of the compound N-(3,5-dimethylphenyl)-N'-(2-trifluoromethylphenyl) guanidine of formula (I) as defined in claim 9, for use in the treatment of a condition mediated by Rho-GTPase cell proteins.

* * * * *